United States Patent [19]

MacMahon et al.

[11] Patent Number: 5,549,699
[45] Date of Patent: Aug. 27, 1996

[54] BONY FIXATION AND SUPPORT OF A PROSTHESIS

[75] Inventors: Edward B. MacMahon, Middleburg, Va.; Mark Forte, Pine Brook, N.J.

[73] Assignee: Osteotech of Virginia, Middleburg, Va.

[21] Appl. No.: 327,661

[22] Filed: Oct. 21, 1994

[51] Int. Cl.⁶ .................................................. A61F 2/34
[52] U.S. Cl. .............................................. 623/22; 623/18
[58] Field of Search ................................ 623/16, 18, 19, 623/22, 23

[56] References Cited

U.S. PATENT DOCUMENTS

| | | | |
|---|---|---|---|
| 3,228,393 | 1/1966 | Michele | 623/23 |
| 3,740,769 | 6/1973 | Haboush | 623/23 |
| 4,535,487 | 8/1985 | Esper et al. . | |
| 4,673,409 | 6/1987 | Van Kampen . | |
| 4,714,470 | 12/1987 | Webb, Jr. et al. . | |
| 4,778,469 | 10/1988 | Lin et al. . | |
| 4,863,474 | 9/1989 | Brown et al. . | |
| 4,959,072 | 9/1990 | Morscher et al. | 623/22 |
| 5,021,063 | 4/1991 | Tager | 623/22 |
| 5,108,432 | 4/1992 | Gustavson . | |
| 5,139,522 | 8/1992 | Adrey et al. | 623/23 |
| 5,171,287 | 12/1992 | Willert et al. | 623/22 |
| 5,192,283 | 3/1993 | Ling et al. | 606/93 |
| 5,314,488 | 5/1994 | Hayashi et al. . | |
| 5,314,490 | 5/1994 | Wagner et al. . | |

FOREIGN PATENT DOCUMENTS

| | | | |
|---|---|---|---|
| 0179736 | 4/1986 | European Pat. Off. | 623/22 |
| 482320 | 4/1992 | European Pat. Off. | 623/22 |
| 0649913 | 6/1985 | Switzerland | 623/22 |

OTHER PUBLICATIONS

"Periprosthetic Bone Loss of the Acetabulum," D'Antonio, Classification of Acetabular Defects, pp. 280–282.
Health News, "Hip and Happy," Panel Concludes That Hip Replacement Surgery Is Better Than Ever, The Washington Post, Sep. 20, 1994, p. 9.

*Primary Examiner*—David Isabella
*Attorney, Agent, or Firm*—Whitham, Curtis, Whitham, & McGinn

[57] ABSTRACT

An acetabular cup includes a plurality of bone receiving depressions on its convex exterior surface. Bone, obtained from the femoral head of the hip to be replaced, is morselized and then compressed in the bone receiving depressions. The dense bone on the exterior surface of the acetabular cup serves as a graft and acts as a new subchondral bone. The bony fixation technique may be used on other prosthesis (e.g., shoulders, and the like). Variations in size, shape, depth and distribution of the recesses can be modified to make this form of fixation applicable to all forms of bone/prosthesis fixation.

8 Claims, 4 Drawing Sheets

BONY FIXATION AND SUPPORT OF A PROSTHESIS

BACKGROUND OF THE INVENTION

1. Field of the Invention

The invention is generally related to techniques which improve the bony fixation and support of a prosthesis. The invention has particular application in total hip replacement operations, wherein the technique utilizes an acetabular cup designed to resist loosening and migration.

2. Description of the Prior Art

Total hip replacement (THR) is one of the most beneficial surgical procedures when outcome is analyzed on a cost/quality-adjusted-life year basis (See, Sledge NIH consensus study September, 1994). The operation provides the patient with increased mobility and independence, thus improving overall quality of life. More than 800,000 artificial hips have been implanted in Americans so far. THR is one of the most commonly performed operations in orthopedic reconstructive surgery today. Over 20,000 hip replacements are performed annually in the United States at an annual nationwide cost in the billions. In 1994, the leading problem in THR is the failure of long term fixation of the acetabular component in the pelvis, and, specifically, the inability of the cup to resist loosening and migration. The 120,000 per year rate includes an increasing number of revision surgeries (second operations) due to failure. The total number of THR operations performed in the United States is expected to increase as the population ages and the currently implanted prostheses begin to fail.

FIG. 1 generally shows a hip replacement installed in a human patient. A stem 10 is anchored in the femur 12 and projects a ball (not shown) proximally into an acetabular component 14 that is positioned in the pelvis 16. Many prior art THRs utilize bone cement 13 for fixating the components to bone. Implanting an artificial hip requires surgical removal of the upper end of the femur, and reaming out a portion of the bone in the acetabulum (socket) of the pelvis. A new acetabular cup 14 is then installed in acetabulum and the stem 10 is inserted into the center of the femur 12. The stem 10 is typically a metallic component such as titanium or cobalt/chromium alloy, and the head (not shown) connected to the stem has a highly polished surface to enhance free rotating motion inside the acetabular cup 14. A plastic liner inside the acetabular cup 14, or construction of the entire acetabular cup 14 from plastic components can aid in permitting free motion of the patient's hip.

A common problem with hip replacements is related to loosening of the artificial socket and migration out of the socket into the pelvis. Loosening and migration of the socket results in loss of bone in the acetabulum. Bone loss can occur in the superior, posterior, anterior, or medial direction, all of which are commonly referred to as segmental defects. In addition, a volummetric loss in the bony substance in the pelvis can occur, and this is commonly referred to as a cavitary defect. Loss of bone in the acetabulum eventually requires replacement of the artificial hip because of pain and shortening of the leg. However, due to the loss of bone in the acetabulum, the revision surgery is likely to be less successful than the first surgery and invariably requires a bone graft.

There are many different configurations for both the stem 10 and the acetabular cup 14. For example, U.S. Pat. No. 5,108,432 to Gustavson, U.S. Pat. No. 4,714,470 to Webb et al., U.S. Pat. No. 4,763,409 to Van Kampen, U.S. Pat. No. 4,778,469 to Lin et al., U.S. Pat. No. 4,535,487 to Esper et al., U.S. Pat. No. 4,863,474 to Brown et al., and U.S. Pat. No. 5,021,063 to Tager all disclose variations on the stem 10 section of a hip replacement, and U.S. Pat. No. 5,171,287 to Willert et al., U.S. Pat. No. 5,314,488 to Hayashi et al., and U.S. Pat. No. 5,314,490 to Wagner et al. all show variations on the acetabular socket. These patents reflect the commonly believed concept that the primary goal of the prosthesis-bone interface is fixation and adherence of one surface to another.

SUMMARY OF THE INVENTION

It is an object of this invention to provide an acetabular cup which will resist loosening and migration.

It is another object of this invention to use compressed bone on the exterior surface of a prosthesis, such as an acetabular cup or femoral stem, to increase the strength of attachment fixation and to provide for improved support of the prosthesis.

It is yet another object of this invention to provide an acetabular cup which is specifically designed to withstand loading, wedging, and torque stresses, and, hence, resist loosening and migration.

According to the invention, it has been recognized by the inventors that the most important issue in THR failure is not related to fixation or adherence problems, but rather is one of lack of bone mass to support the stiff prosthetic cup. This invention proposes a hemispherically shaped acetabular cup with an outer shell having a series of recesses over its convex surface. During total hip replacement, the femoral head is retrieved, morcelized with a bone mill, and then compressed into the recesses on the convex surface of the acetabular cup. The dense bone fitted into the recesses of the acetabular cup acts as a bone graft and serves as a new subchondral bone in the acetabulum. Thus, the dense bone allows the acetabular cup to withstand loading, wedging, and torque stresses. Preferably, the dense bone occupies greater than 50% of the exposed area on the convex surface of the acetabular cup so that an abundance of bone will be available for grafting. The recesses on the convex surface can be of variable depth, shape and size; however, in a preferred embodiment the recesses are progressively deeper in the sites subjected to the greatest compressive loads. Having increased bone mass strategically located at the sites of higher compressive loads helps resist loosening and migration of the acetabular cup, and mimics the natural structure of the acetabular subchondral plate.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
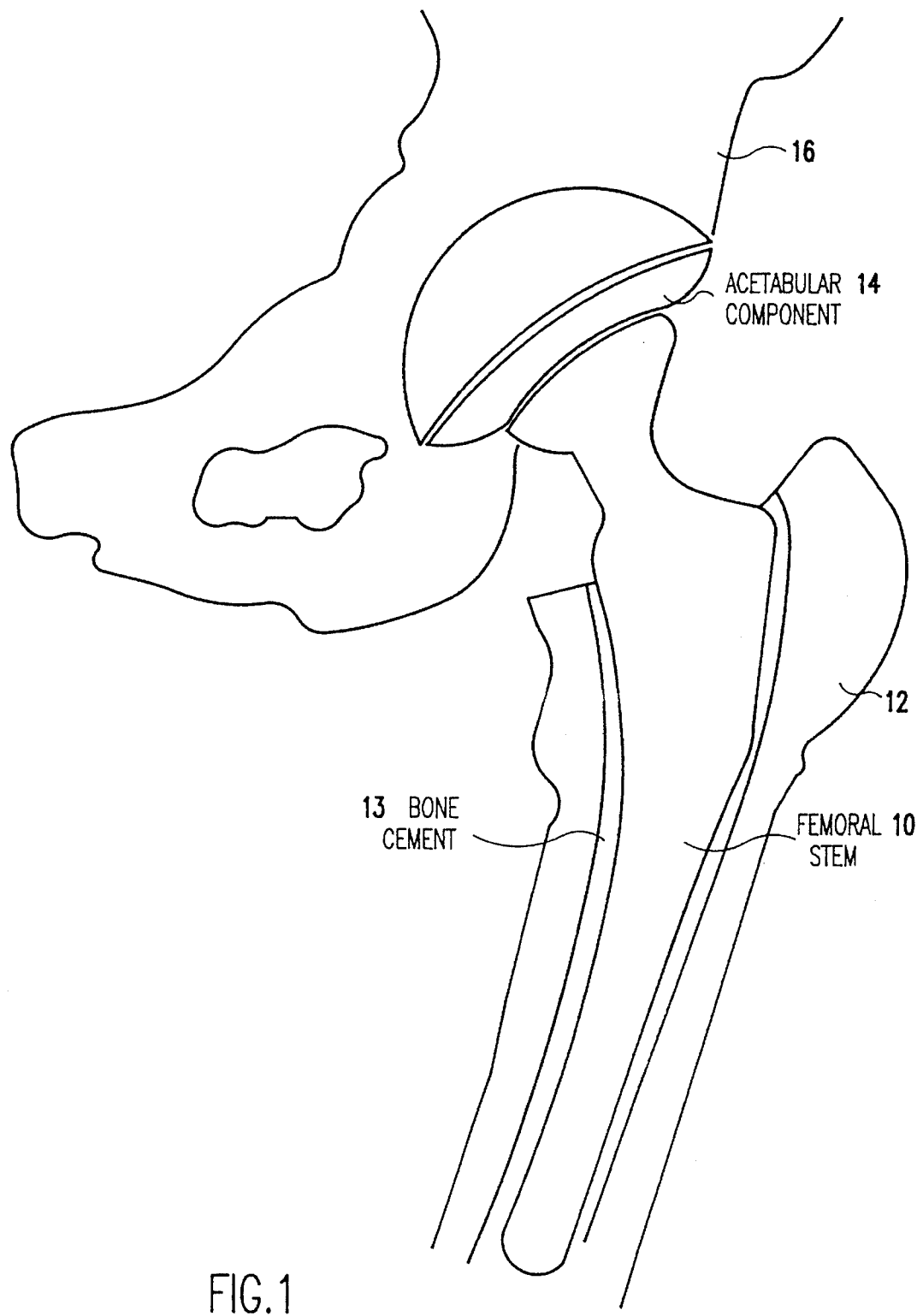
FIG. 1 is a generalized cross-sectional view of an artificial hip replacement.

An explanation of how an acetabular cup migrates in the acetabulum and, hence, a possible solution to the problem, lies in an understanding of how normal forces are tolerated on the pelvis during weight bearing and how total hip arthroplasty changes these conditions.

The acetabulum is not a simple hole in the side of the pelvis. A study of its evolution in the animal kingdom reveals the principles of how its structure has been modified by the functional needs of the animal. In all animals including humans, the acetabulum is never a hemisphere like the prosthetic cup that is inserted in THR. Instead, it is a horse shoe shaped cavity with a tension band system joining the ends. The opening between the ends of the horse shoe shape is always directed towards the obturator foramen. This design implies that during the loading and unloading which occurs during walking the socket springs open and closes to distribute the stresses more evenly. When this system is sacrificed as it is in THR, loading stresses are likely to predominate in one area.

When man assumed the upright position, the pelvis was required to rotate from the horizontal position of the quadrupeds to a vertical position. This resulted in a change in direction of the gravitational and muscle forces that are applied to the pelvis. Because the pelvis of the quadruped supported only part of the body weight and was used for forward propulsion, it is composed of hard cortical bone. In humans, an extensive shock absorbing system became mandatory. The change of the pelvis from cortical bone to cancellous bone was only part of a larger system that included a longer femoral neck that bends, much larger intervertebral disc spaces and a multicurved spine. The acetabulum participates in this process. Three swollen areas of cancellous bone appear to supplement the functions of the horse shoe shape. These areas are called the acetabular metaphyses, and their importance is that the superior and posterior ones correspond to the sites of migration of the cup. Medial migration occurs when there was a pre-existing narrowing of the medial wall or from surgical reaming at the time of the primary surgery.

The evolutionary change of the pelvis from dense cortical bone to softer more compliant cancellous bone in humans, enables the study of stress trajectories, as was first described by Wolff in 1892. A detailed examination of these patterns in the human is presented in Holm, *Acta Orthopedica Scand.* 51, 1980. In analyzing the curved roof of the acetabulum, Holm used the effects of applying even stresses to the concave surface of the curved beam as a mechanical analogy. Vertical trajectories radiate upwards and outward, being connected to one another by horizontal tension bands. In the pelvis, the bone densities are greatest in an arc that extends from the superior acetabulum to the sacro-iliac joint (see, Dalstra, *J. of Biomechanics*, 26, 1993). This design is an example of what is called a post and lintel system, an example being the ancient monument at Stonehenge. The subchondral plate is the lintel and the trajectories are the posts. When the strong subchondral plate is absent, there is little remaining to prevent collapse and migration. When osteoarthritis of the hip has been present for many years osteoporosis can be present in the pelvis and the subchondral plate not hemispherical. After THR, the physiological bending of the femoral neck and the impact dampening capacity of the femoral head are both lost. Impact from weight bearing is then transmitted directly from the stiff femoral diaphysis directly onto the acetabulum.

The fatigue behavior of bone is characterized by gradual loss of stiffness due to fatigue damage accumulation from the cyclical loading (see, Choi and Goldstein, *J. of Biomechanics* 25, 1992). Decrease in either quantity or quality of bone will predispose to failure. Density of bone is equivalent to the combination of these two properties and compressive strength of cancellous bone is a function of density. This relationship has been well studied. At densities less than 350 $Kg/m^3$, the slope of a graph plotting density against compressive strength is 2; whereas, when the density is above this figure, the slope increases to 3. Also, when a confining ring is used, as in the case of the present invention, the strength is raised further by a third (see, Gibson, *J. or Biomechanics*, 18, 1985). In order to obtain this degree of compressibility, one would need a force of 150 $lbs/in^2$ (10 $NM/m^2$) for two minutes; a force that can easily be applied manually to morcelized bone. The Tracer Bone Mill is a hand or power operated tool that can cut a femoral head into 2, 4, or 6 mm chips within two minutes. In respect to the present invention, the milling and later compression of the graft into the shell should take a maximum of ten minutes and can be performed while the surgeon is preparing the femoral canal and acetabulum.

To date, the designs of the acetabular socket have focused on the issue of fixation and adherence. Cement fixation produces effective adherence, especially if pressurized. However, since it is in one rigid piece, the shift in direction of force that is associated with hip flexion during walking will tend to tilt the cement back and forth (see, Davy, NIH THR Concensus 1994). This can explain why newer cement techniques have benefited femoral stem fixation, but not the acetabular side (see, Callaghan, *J. Bone and Joint Surg.*, 1994). Porous coated acetabular components were introduced because of the comparatively high rate of loosening and migration in the cemented components. However, a recent study from Boston that reflected the current state of the art with five year follow-up revealed that over one third of the cases had radiolucent lines between the porous cup and cancellous bone bed (see, Schmalzried, *J. of Bone and Joint Surg.*, 74A, 1992)

Sir John Charnley who is the father of THR predicted thirty years ago that the long term problem with this procedure would be on the acetabular side.

In this invention, the inventors have determined that a significant cause of loosening and migration of the acetabular component is the consequence of an inadequate bone stock unable to withstand the cyclical impact of hard cement or metal. Since bone graft is usually required in revision cases and the femoral head is no longer available; it is proposed that if bone graft is part of the solution to revision surgery, bone graft should be part of the prevention. The invention rectifies this imbalance by creating a compressed cancellous bone barrier through which the stresses from the femur must pass before being transmitted into the acetabulum. In this way, the subchondral plate or lintel is restored.

In the present invention, the inventors have identified that the negative changes produced in the acetabulum by total hip arthroplasty are the direct consequence of an inadequate bone stock loaded with materials too stiff for the acetabulum to be able to withstand over a long period of cyclical loading. Several effects of this mismatch result. First, the subchondral bone sector of the pelvic cortical shell is broached or removed by reaming; thus, some area of the cancellous bone of the pelvis is no longer "contained" and, therefore, is exposed to local pressure at the implant/bone interface. Second, there is often poor contact between the surface of a porous coated acetabular cup and the bone; allowing weak fixation and a space for entry of particle debris. This gap has additional importance in that porous coating tends to form a fibrous union with small gaps and micromotion. Autogenous bone graft will unite with greater gaps and micromotion. Third, as is standard in large joints, the concave acetabular subchondral plate is normally thicker than the convex subchondral plate at the femoral head. Also, the height of the plate is not uniform throughout the acetabulum and sphericity is altered in osteoarthritis. Reaming can only further increase the insufficiency of the subchondral plate. Fourth, the surface of the relatively compliant cancellous bone is exposed to direct compressive stresses from the interposed cement or the metal cup shell. Fifth, the hemispheric geometry of the acetabular cup lacks rotational stability so that the cancellous bone-prosthesis interface is exposed to higher shear stresses from the greater magnitude of frictional torque of the acetabular prosthesis bearing surface.

In the present invention, loosening and migration of the acetabular cup is prevented by using the femoral head as a bone graft to create the equivalent of a new subchondral bone at the time of surgery. In particular, during total hip replacement surgery, the femoral head is retrieved and morcelized. The retrieval and morcelizing operations can be accomplished using conventional tools and techniques. For example, the first step in THR is removal of the femoral head and neck by cutting through the neck with an oscillating saw. The excised tissue is then placed in a bone mill, such as the Tracer Bone Mill, which converts the bone into chips. The Tracer Bone Mill can convert the femoral head and neck into 2–6 mm bone chips, depending on the choice of the physician, within a matter of minutes. The shell can accept the different size chips depending on the depth of the recess.

The morcelized bone is then compressed into recesses on the convex surface of the acetabular cup. Compacting the morselized bone into the recesses can be achieved in the following way. Ideally, the inverted acetabular cup is placed on top of a matching ball so that the convex surface of the cup faces upwards. A cup shaped template with holes that correspond to the prosthesis recesses is then placed on top of the prosthesis and the holes are manually filled with appropriate sized chips. The chips are then compressed with an plunger so that the top of the graft is level with the edge of the shell. As discussed above, applying a force of approximately 150 lbs/in$^2$ for two minutes is sufficient to compact the bone chips and to form dense bone (>350 Kg/m$^3$) in the recesses. The acetabular cup is then implanted into the acetabulum of the patient and the leg is connected using a stem and ball component similar to that shown in FIG. 1.

Figure 2A:
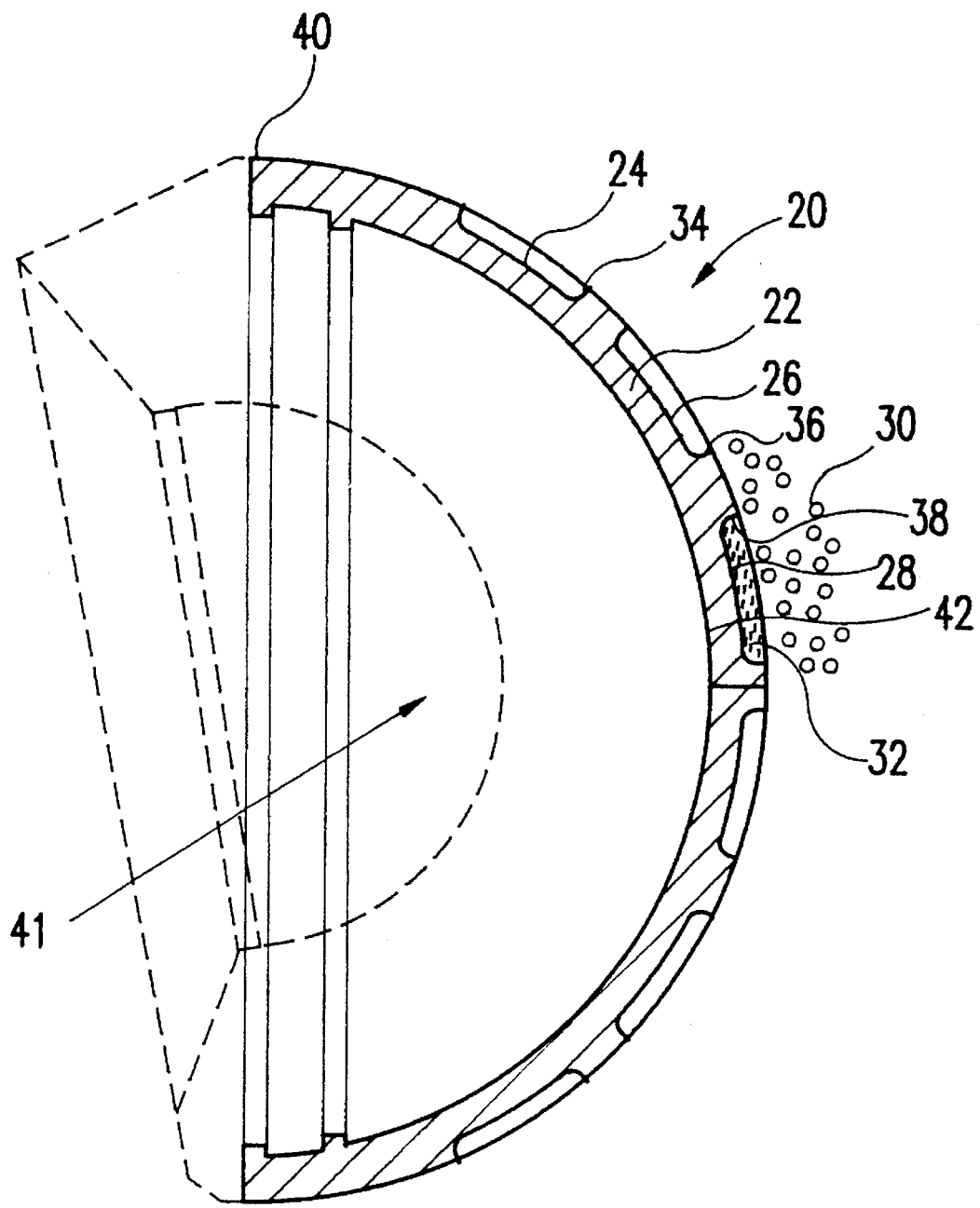
FIGS. 2a and 2b are top and cross-sectional side views of an acetabular cup according to the present invention.
Figure 2B:
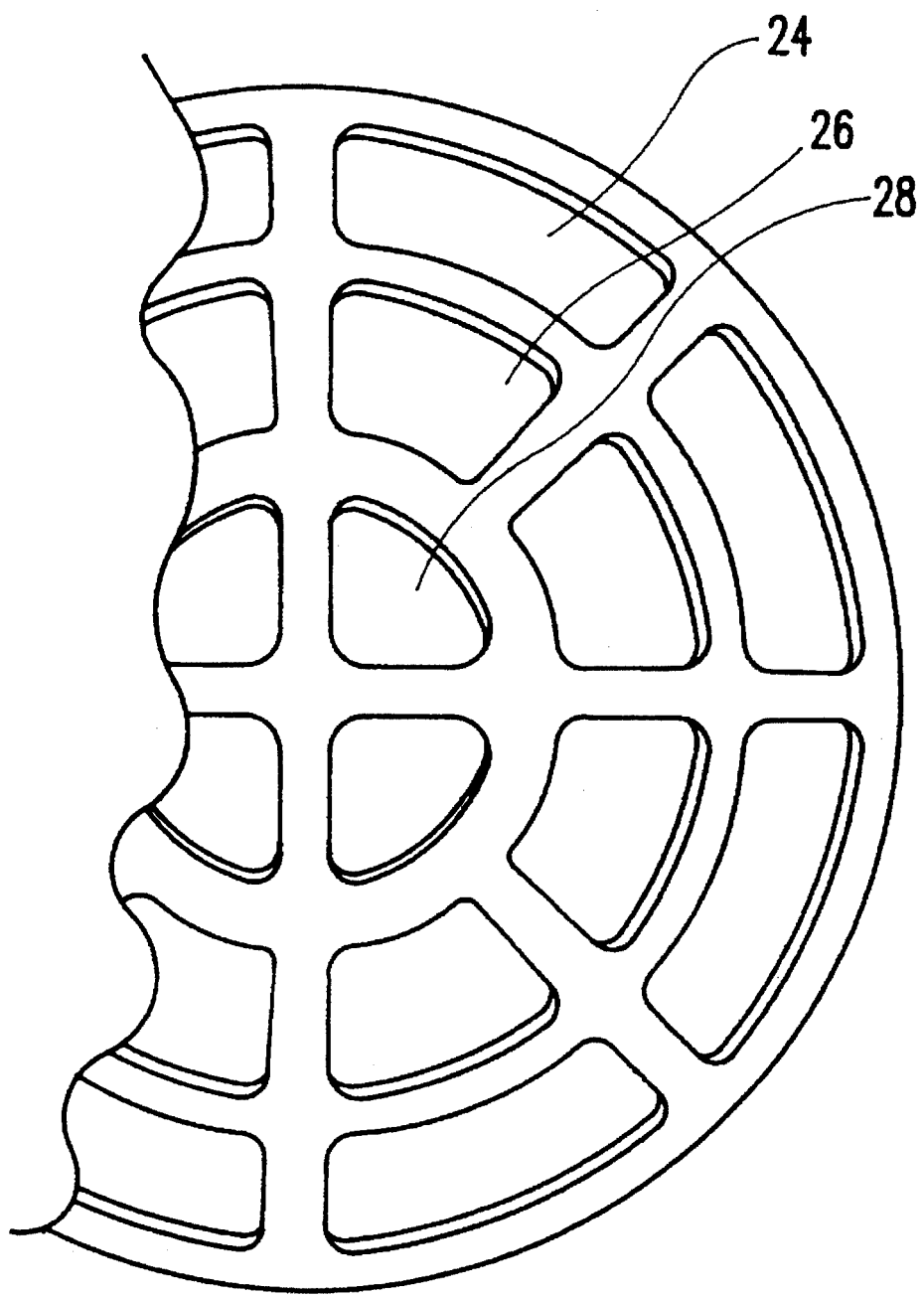

FIGS. 2a and 2b show a preferred embodiment for the acetabular cup of this invention. The acetabular cup 20 is hemispherically shaped and has an external shell 22 that has a plurality of bone receiving depressions, which are indicated generally as 24, 26, and 28. Prior to implantation of the acetabular cup 20, morcelized bone 30, preferably from the femur head, is compressed into each of the bone receiving depressions 24, 26, and 28. Preferably, the morcelized bone 30 is compacted to a point where the morcelized bone 30 assumes the nature of dense bone 32 (>350 Kg/m$^3$). As discussed above, this can be accomplished by adding 2–6 mm bone chips obtained from milling the femoral head to the recesses and then using a plunger to compact the chips at an applied force of 150 lbs/in$^2$. Other techniques for filling the recesses and forming dense bone could be used within the practice of this invention. Preferably, the bone is compacted to a level even with the surface of the shell.

The bone receiving depressions 24, 26, and 28, can be of varying sizes and shapes. They do not need to be of uniform geometrical size and shape as shown in FIG. 2b. However, as is shown in FIG. 2b, it is preferable that the bone receiving depressions 24, 26, and 28 occupy greater than 50% of the total surface area on the convex outer surface of the shell 22. Since the goal of the design is to rectify the loss of supporting bone, the area of bone graft surface should be a majority as a proportion of the cup surface.

The acetabular cup design also allows a wide variety of shapes, sizes and depths of the recesses to be made on the shell convex surface. Different shapes, sizes, and depths may be selected to address the different directions in which the prosthesis may tend to migrate. There are three acetabular metaphyses and a medial wall that must resist the stresses applied from the femoral head. Clinically, migration of the cup mostly occurs medially, superiorly, or posteriorly. After the end of reaming, the surgeon can evaluate which direction migration is most likely to occur. Once this is established, a cup is selected which will have increased dense bone matter in the direction the cup is most likely to migrate.

FIG. 2a shows that the bone receiving depressions 24, 26, and 28 can be of varying depths at different sites on the surface of the shell 22. In the preferred embodiment, shown in FIG. 2a, the sidewall 34 extending from the base of depression 24 is smaller than the sidewall 36 extending from the base of depression 26, which, in turn, is smaller than the sidewall 38 extending from the base of depression 28. Having progressively deeper depressions on the convex surface in the rim 40 to base 42 direction assures that greater thicknesses of bone are present at a region of high joint loading; and mimics the natural structure of the previous subchondral plate.

While FIG. 2a shows an acetabular cup which includes more bone matter at the base than at the rim regions. This configuration is most suited for situations where the acetabular cup is likely to migrate medially. In the situations where the acetabular cup is likely to migrate in a superior or posterior direction, the depths of the recesses may be larger on one side of the cup compared to the base or other sides of the cup. In this way, a cup with relatively more bony matter oriented in the direction the cup is most likely to migrate would be installed in the patient.

The shell 22 of the acetabular cup 20 can be made from ceramics, or plastics such as high density polyethylene; however, it is preferable to use metals or metal alloys including cobalt/chrome alloys, titanium alloys, and the like.

The shell 22 preferably has a sizing radius ranging between 22 mm and 35 mm in order to fit within the natural variation of the human acetabulum. Slightly larger sizes may be used in cases where bone losses have occurred. In addition, if the acetabular cup 20 is to be used in animals, such as dogs, the radius of the shell 22 should be sized to fit in the acetabulum of the particular species being treated.

The socket bearing portion 41 of the acetabular component 20 will generally have a hemispherical geometry. Preferably, the size of this hemispheric bearing surface 41 will be 22, 26, 28, or 32 mm in diameter. "Low" friction joint arthroplasty is obtained by a tight fitting interface between the bearing surface 41 and the highly polished spherical head of the femoral component. Other materials such as metal ball/metal socket, metal ball/ceramic socket, ceramic ball/ultra high molecular density polyethylene socket, ceramic on ceramic, etc., can also be employed.

Figure 3:
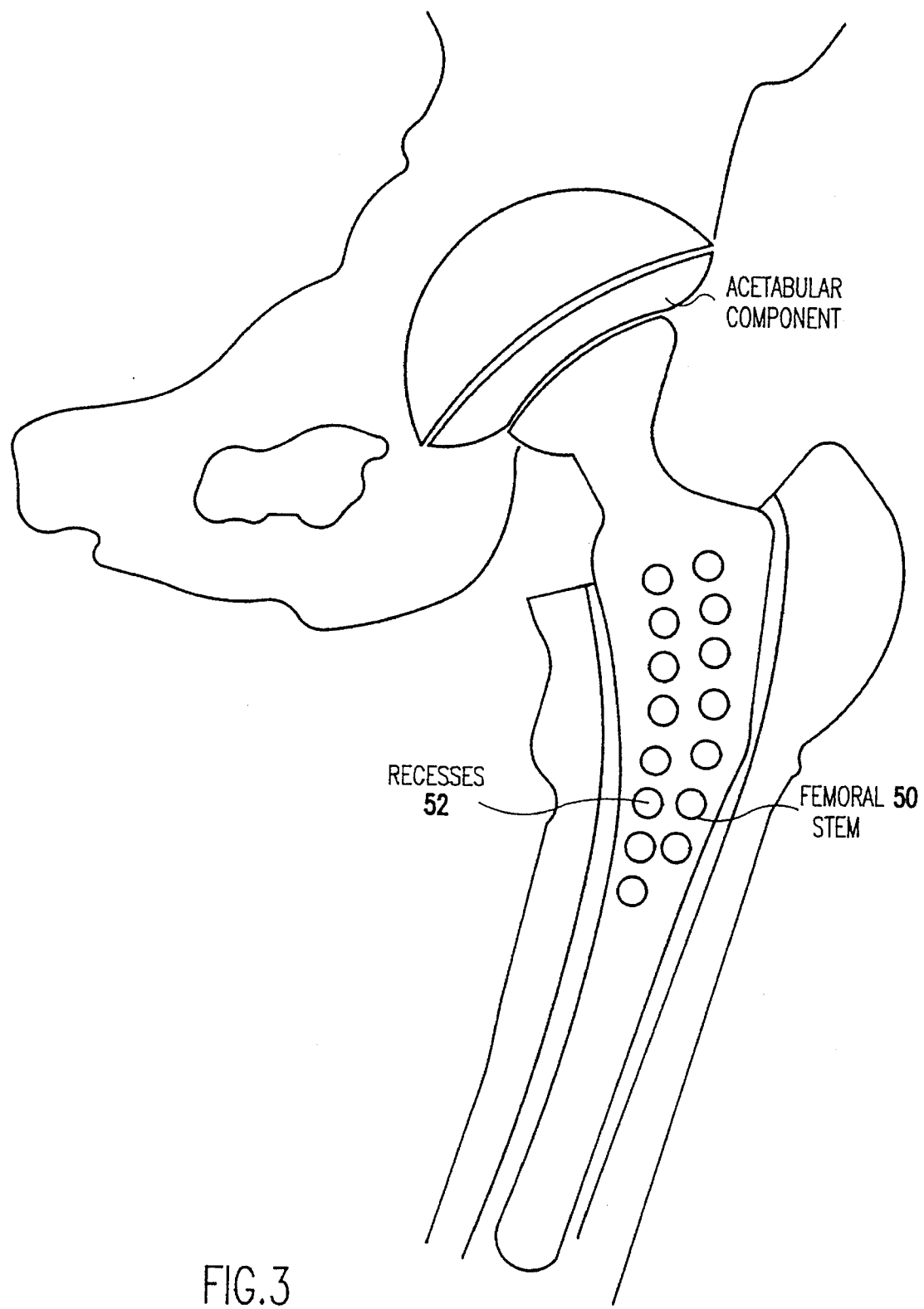
FIG. 3 is a side view of the femoral stem according to the present invention.

FIG. 3 shows a femoral hip stem 50 which includes a plurality of recesses 52 along its surface. As discussed above in connection with the acetabular cup, compressing cancellous bone, which can be obtained from the femur head or other sources, into the recesses 52 provides a dense bone (>350 Kg/m$^3$) barrier through which stresses from the femur must pass and provide a superior interface between the bone and prosthesis.

The bony fixation technique described above for THR may be used on other prosthesis (e.g., shoulders, and the like). Variations in size, shape, depth and distribution of the recesses can be modified to make this form of fixation applicable to all forms of bone/prosthesis fixation.

While the invention has been described in terms of its preferred embodiments, those skilled in the art will recognize that the invention can be practiced with modification within the spirit and scope of the appended claims.

We claim:

1. An acetabular cup, comprising:

a shell having a concave inner surface and a convex exterior surface; and a plurality of bone receiving regions positioned on said convex exterior surface of said shell, each of said bone receiving regions having a base and side walls, and said side walls of bone receiving regions positioned relatively closer to a base of said shell are relatively deeper than sidewalls of bone receiving regions positioned relatively closer to a rim of said shell, wherein said plurality of bone receiving regions retentively contain compacted bone chips, and wherein said plurality of bone receiving regions cover a majority of said convex exterior surface of said shell.

2. The acetabular cup of claim 1 wherein said shell is hemispherically shaped.

3. A method for installing an acetabular cup during total hip replacement surgery, comprising the steps of:

surgically reaming the acetabulum of a patient;

determining a direction of migration an acetabular cup is most likely to travel when installed in said acetabulum, wherein said acetabular cup comprises a plurality of bone receiving regions on said external shell of said acetabular cup, each of said bone receiving regions having a base and side walls, and each of said bone receiving regions being capable of accepting said bone chips and capable of retaining said bone chips after being compacted within said bone receiving regions to form dense selecting said acetabular cup with bone receiving regions capable of accepting and retaining relatively larger amounts of dense bone on a portion of said external shell compared to other portions of said external shell which corresponds to said direction of migration determined during said determining step;

recovering a femoral head from said patient;

milling said femoral head to produce cancellous bone chips;

compacting said cancellous bone chips into said plurality of bone receiving regions on said external shell of said acetabular cup; and installing said acetabular cup into said acetabulum of said patient.

4. The acetabular cup of claim 1 wherein said compacted bone chips are contained in said plurality of bone receiving regions in a quantity effective to level even with said convex exterior of said shell.

5. The acetabular cup of claim 1 wherein said bone chips each have a size ranging from 2 to 6 mm.

6. The acetabular cup of claim 1 wherein said sidewalls of each of said bone receiving regions are oriented substantially perpendicularly to said base of said bone receiving region.

7. The method of claim 3 wherein said external shell further comprises rim regions and a base, and said cup selecting comprises providing relatively larger amounts of dense bone at said base than said rim regions.

8. The method of claim 3 wherein said external shell further comprises a base and rim regions traversing a plurality of different sides of said cup, and said cup selecting comprises providing relatively larger amounts of dense bone at one of said rim regions at one side of said cup than at a different rim region at a different side of said cup.

* * * * *